United States Patent [19]
Gopalkrishnan et al.

[11] Patent Number: 5,855,874
[45] Date of Patent: Jan. 5, 1999

[54] DENTIFRICE FORMULATIONS CONTAINING LIQUID POLYOXYALKYLENE COMPOUNDS MISCIBLE IN A LIQUID, POLYALKYLENE GLYCOL CARRIER

[75] Inventors: Sridhar Gopalkrishnan, Gross Ile, Mich.; Richard Holland, Flanders, N.J.

[73] Assignee: BASF Corporation, Mount Olive, N.J.

[21] Appl. No.: 774,663

[22] Filed: Dec. 30, 1996

[51] Int. Cl.⁶ ............... A61K 7/16; A61K 7/18; A61K 7/20

[52] U.S. Cl. ............... 424/52; 424/49; 424/55

[58] Field of Search ............... 424/49–58

[56] References Cited

U.S. PATENT DOCUMENTS

| | | |
|---|---|---|
| 3,639,574 | 2/1972 | Schmolka . |
| 3,740,421 | 6/1973 | Schmolka . |
| 3,867,533 | 2/1975 | Schmolka . |
| 4,272,394 | 6/1981 | Kaneko . |
| 4,411,810 | 10/1983 | Dutton . |
| 4,465,633 | 8/1984 | Schmolka . |
| 4,465,663 | 8/1984 | Schmolka . |
| 4,476,107 | 10/1984 | Schmolka . |
| 4,925,988 | 5/1990 | Licht et al. . |
| 5,035,880 | 7/1991 | Mori et al. . |
| 5,057,307 | 10/1991 | Hill et al. . |
| 5,073,368 | 12/1991 | Subramaniam . |
| 5,096,698 | 3/1992 | Mitchell et al. . |
| 5,187,191 | 2/1993 | Otten et al. . |
| 5,256,396 | 10/1993 | Peichota . |
| 5,374,368 | 12/1994 | Hauschild . |
| 5,424,060 | 6/1995 | Hauschild . |
| 5,496,542 | 3/1996 | Hauschild . |

FOREIGN PATENT DOCUMENTS

| | | |
|---|---|---|
| 0 546 627 A1 | 6/1993 | European Pat. Off. . |
| WO 93/13750 | 7/1993 | European Pat. Off. . |
| 47-48366 | 12/1972 | Japan . |
| 546-627 | 6/1991 | United Kingdom . |
| WO 93/13750 | 7/1993 | WIPO . |

OTHER PUBLICATIONS

BASF Performance Chemicals Product Brochure; BASF Corporation; May 1997; Mount Olive, New Jersey.

*Primary Examiner*—Shep Rose
*Attorney, Agent, or Firm*—Joanne P. Will

[57] ABSTRACT

A dentifrice composition comprising a liquid polyalkylene glycol carrier, and a liquid polyoxyalkylene compound miscible in said liquid polyalkylene glycol carrier.

5 Claims, No Drawings

DENTIFRICE FORMULATIONS CONTAINING LIQUID POLYOXYALKYLENE COMPOUNDS MISCIBLE IN A LIQUID, POLYALKYLENE GLYCOL CARRIER

FIELD OF THE INVENTION

The present invention relates to an oral care formulation comprising a liquid, polyalkylene glycol carrier and a liquid polyoxyalkylene compound miscible in said liquid, polyalkylene glycol carrier.

BACKGROUND

Polyoxyalkylene block copolymers are well known to those skilled in the non-ionic surfactant art. Specifically, U.S. Pat. No. 3,740,421 (Schmolka) assigned to BASF discloses aqueous gels prepared using a block copolymer of polyoxyethylene/polyoxypropylene suitable for pharmaceutical and personal care compositions. U.S. Pat. No. 3,639,574 (Schmolka) assigned to BASF discloses polyoxyethylene/polyoxypropylene block copolymers as gelling agents for hydrogen peroxide compositions. U.S. Pat. No. 4,465,663 (Schmolka) assigned to BASF discloses polyoxybutylene/polyoxyethylene block copolymers as gelling agents for aqueous gels useful in personal care and pharmaceutical applications. These compounds are sold by the BASF Corporation under the PLURONIC® tradename.

Additionally, U.S. Pat. No. 4,272,394 and U.S. Pat. No. 4,411,810 disclose the use of polyoxyalkylene block copolymers in machine dishwashing applications. U.S. Pat. No. 4,925,988 discloses a nonionic surfactant employing a specific combination of alkanol, ethylene oxide and propylene oxide useful in an automatic dishwashing application. U.S. Pat. No. 5,374,368 describes the use of liquid EO/PO/EO triblock co-polymers (PLURONIC® L 31 and L 35 surfactants) in stable hydrogen peroxide releasing dental care compositions at levels of 55–90% by weight of the dental care composition. U.S. Pat. No. 3,740,421 discloses gel forming solid EO/PO/EO triblock copolymers useful in cosmetic and personal care formulations at levels of approximately 20–25% by weight. Preferred solid EO/PO/EO triblock copolymers have a molecular weight of 4,600–16,000. Said solid EO/PO/EO triblock copolymers form a gel when added to an aqueous solution. U.S. Pat. No. 3,867,533 discloses aqueous gel compositions containing solid EO/PO/EO triblock copolymers, having a molecular weight of 6,450–20,000 useful at levels of approximately 20% by weight. Said compositions are useful in preparing cosmetic formulations. U.S. Pat. No. 4,465,663 discloses clear aqueous cosmetic gels containing solid EO/BO (butylene oxide)/EO triblock copolymers at levels of approximately 20%. U.S. Pat. No. 5,035,880 discloses a stable dentifrice compositions containing a cetylpyridinium bactericide and EO/PO/EO solid triblock copolymers (PLURONIC® F 127 surfactant), and polyethylene glycol at levels of 15–80% by weight. U.S. Pat. No. 4,476,107 discloses a mouthwash containing EO/BO(butylene oxide)/EO triblock copolymers at levels of 0.5–5.0% by weight. U.S. Pat. No. 5,057,307 discloses oral hygiene gels containing non-ionic surfactants, coating substances; and viscosifiers. Said non-ionic surfactants are the PLURONIC® F 108 and F 127 surfactants available from BASF Corporation, Mt. Olive, N.J. U.S. Pat. No. 5,256,396 discloses a topical composition comprising an EO/PO/EO solid triblock copolymer (PLURONIC®) F 127 surfactant) used at a level of more than 10% to about 17% by weight. EPO-546-627A discloses mouthwash compositions comprising solid EO/PO/EO triblock copolymers such as PLURONIC® L 108, F88 surfactants at levels of 0.5–3% by weight. U.S. Pat. No. 5,073,368 discloses mouthwashes containing solid EO/PO/EO triblock copolymers such as PLURONIC(® F 87 surfactant at levels of 0.1–3% by weight. WO 93/13750 discloses an ocular cleansing composition comprising solid PLURONIC® F 87 and paste PLURONIC® P 85 EO/PO/EO triblock copolymers. PLURONIC(® P 85 surfactant is 4–9% by weight of the cleansing composition, PLURONIC® F 87 surfactant is 0.5–2% by weight of the cleansing composition. Finally, U.S. Pat. No. 5,096,698 discloses a dental creme composition containing a non-ionic triblock liquid EO/PO/EO copolymer or a solid triblock EO/PO/EO copolymer at levels of 0.1–5% by weight. Said copolymers help to prevent phase separation. PLURONIC® F 108 surfactant (solid) is most preferred, followed by PLURONIC® F 87, PLURONIC® F 127, and PLURONIC® L 72 surfactants. U.S. Pat. No. 4,272,394 discloses novel, low-foaming nonionic surfactant for machine dishwashing compositions. U.S. Pat. No. 4,411,810 discloses a low foaming, low cloud point, nonionic surfactant for machine dishwashing compositions. JP 47-48366 B4 discloses a process for producing tasteless, liquid, heteric polyoxyalkylene compounds of molecular weight 1000 or higher. U.S. Pat. No. 5,187,191 discloses polyoxyalkylene block copolymers in agricultural formulations. U.S. Pat. No. 5,496,542, U.S. Pat. No. 5,374,368, and U.S. Pat. No. 5,424,060 disclose the use of polyoxyalkylene compound for formulating a stable percarbonate formulation as well as a dentrifice composition.

The present invention relates to oral care compositions, such as dentrifice formulations. Dentrifice formulations typically contain substantial amounts of humectants. Humectants help the formulation retain its moisture, thus, preventing the formulation from hardening when the container cap is left open for extended periods. Typical humectants employed in such formulations are glycerol, sorbitol which are usually the preferred humectants because of their sweet taste. Other humectants which are also used are polyethylene glycols of low molecular weight typically between 200–600. Liquid polyethylene glycols constitute an excellent choice as a carrier for formulating a non-aqueous, dentrifice formulation since they come with several advantages such as good hygroscopicity, low viscosity, good compatibility with several dentrifice ingredients, low volatility, low cost, low toxicity, low odor and low pour point. More recently, toothpaste compositions are being formulated without any significant incorporation of water. Examples of such toothpaste compositions are those that cannot tolerate the presence of significant levels of water due to concerns related to decomposition of key ingredients leading to loss of activity, or reactivity of ingredients, for example, baking soda and a peroxygen compound such as, hydrogen peroxide or sodium percarbonate. The formulation and increased stability of such toothpaste compositions is achieved by employing a non-aqueous carrier typically selected from low molecular weight liquid polyethylene glycols. Dentrifice formulations also contain an anionic surfactant, typically selected from sulfate esters of $C_{10-18}$ alcohols. An example of such a anionic surfactant is sodium lauryl sulfate. The primary function of the anionic surfactant is to provide efficient foaming action during brushing. However, in many instances the foaming action provided by the anionic surfactant alone is inadequate and often additional ingredients have to be added in combination with the anionic surfactant to achieve the desired foam profile during brushing. A common ingredient that is typically selected to achieve additional foam boosting are the high molecular weight, solid block copolymers of ethylene oxide and propylene oxide. Examples of such solid block copolymers are those that have a number average molecular weight over 8000 and also contain at least 50% ethylene oxide. Particularly preferred are those that contain between 70%–80% ethylene oxide and have a number average molecular weight greater than 9000.

Further, a limitation also exists with the use of the high molecular weight, solid, block copolymers of ethylene oxide and propylene oxide in a non-aqueous dentrifice formulation because they are insoluble in the liquid polyalkylene glycol carrier. Dissolution of the solid block copolymer in the liquid polyalkylene glycol carrier is achieved by heating the two components until a single clear phase is achieved. Unfortunately, upon cooling back to ambient temperatures, the solid block copolymer has a tendency to phase separate leading to the formation of a heterogenous mixture. The formation of a heterogenous phase is particularly problematic since it may lead to a preferential partitioning of certain dentrifice components in any one phase and an altering of the homogenity of the formulation. This altering of the homogenity of the formulation is particularly noticeable when the dentrifice formulation undergoes multiple heating and cooling cycles during transportation and storage.

The Applicants have solved these aforementioned problems in the art. Surprisingly, Applicants have discovered that if the solid block copolymers are rendered liquid during their preparation, by addition of small amounts of a $C_3$ or higher alkylene oxide to the crystalline, hydrophilic portion of the solid block copolymer to produce a liquid polyoxyalkylene compound of similar hydrophilicity and molecular weight, then a single, clear, homogenous phase is achieved upon adding to the liquid, polyoxyalkylene glycol carrier. An additional advantage with the use of the high molecular weight liquid polyoxyalkylene compounds of this invention is that upon addition to the polyalkylene glycol carrier, they are readily miscible and form a clear, homogenous, single phase composition, and do not have to be heated to achieve dissolution.

SUMMARY

A dentrifice composition comprising:

(a) a liquid polyalkylene glycol carrier and;

(b) a liquid polyoxyalkylene compound miscible in said liquid polyalkylene glycol carrier, wherein said:

liquid polyalkylene glycol carrier (a) is selected from:
(i) liquid polyethylene glycols having a molecular weight of no more than about 600; or
(ii) liquid polyoxyalkylene glycols having a molecular weight greater than 600 and less than about 3000 of Formula I or mixtures of (i) and (ii):

I-[(EO)$_a$(AO)$_b$-M]$_x$;  Formula I wherein in Formula I,I is an initiator or a mixture of initiators having at least two carbon atoms and at least two or more hydroxyl substituents;
AO is a $C_{3-4}$ alkylene oxide or a mixture of $C_{3-4}$ alkylene oxides;
EO is ethylene oxide;
wherein, further EO and AO can be distributed randomly and/or arranged in a block sequence.
M is Hydrogen or an alkali metal or alkaline earth metal;
a is an integer from about 6–22;
b is an integer from about 1 to 9;
x is an integer from about 2 to 4;
and further provided that;
said liquid polyoxyalkylene compound (b), which is miscible in (a), is represented by Formula II:

I[(AO)$_a$-(XO)-M]$_x$  Formula II wherein in Formula II:
I is an initiator or a mixture of initiators having at least two carbon atoms and two hydroxyl substituents;
AO is a $C_{3-4}$ alkylene oxide or mixtures of $C_{3-4}$ alkylene oxide arranged in a block sequence;
XO is (EO)$_b$(AO)$_c$ wherein EO is ethylene oxide and EO and AO are distributed randomly;
M is hydrogen or an alkali metal or an alkaline earth metal;
a is an integer from 15–35;
b is an integer from 50–150;
c is an integer from 7–90;
x is 2.

The molecular weight of the compound of Formula II is from 8000–28000.

DETAILED DESCRIPTION

A dentrifice composition comprising:

(a) a liquid polyalkylene glycol carrier and;

(b) a liquid polyoxyalkylene compound miscible in said liquid polyalkylene glycol carrier, wherein said:

liquid polyalkylene glycol carrier (a) is selected from:
(i) liquid polyethylene glycols having a molecular weight of no more than about 600; or
(ii) liquid polyoxyalkylene glycols having a molecular weight greater than 600 and less than about 3000 of Formula I or mixtures of (i) and (ii):

I—[(EO)$_a$(AO)$_b$—M]$_x$;  Formula I wherein, in Formula I, I is an initiator or a mixture of initiators having at least two carbon atoms and at least two or more hydroxyl substituents;
AO is a $C_{3-4}$ alkylene oxide or a mixture of $C_{3-4}$ alkylene oxides;
EO is ethylene oxide;
wherein, further EO and AO can be distributed randomly and/or arranged in a block sequence.
M is Hydrogen or an alkali metal or alkaline earth metal;
a is an integer from about 6–22;
b is an integer from about 1–9;
x is an integer from about 2–4;
and further provided that;
said liquid polyoxyalkylene compound (b), which is miscible in (a), is represented by Formula II:

I[(AO)$_a$—(XO)—M]$_x$  Formula II wherein in Formula II:
I is an initiator or a mixture of initiators having at least two carbon atoms and two hydroxyl substituents;
AO is a $C_{3-4}$ alkylene oxide or mixtures of $C_{3-4}$ alkylene oxide arranged in a block sequence;
XO is (EO)b(AO)C wherein EO is ethylene oxide and EO and AO are distributed randomly;
M is hydrogen or an alkali metal or an alkaline earth metal;
a is an integer from 15–35;
b is an integer from 50–150;
c is an integer from 7–90;
x is 2.

The molecular weight range for Formula I is from about 600–3000.

The more preferred values for molecular weight are from about 1000–2500.

The most preferred molecular weight is from about 1500–2000.

The molecular weight of the liquid polyoxyalkylene compound of Formula II is from 8000–28,000, more preferred is from 9000–24,000, and most preferred is from 10,000–19,500.

In Formula I, a is an integer from about 6–22, preferably, from about 7–20 and more preferably from about 10–16; b is an integer from about 1–9, preferably from about 1–7 and more preferably from about 2–5; x is an integer from about 2–4, preferably from about 2–3 and more preferably 2.

In Formula II, a is an integer from 15–35, preferably 20–32, more preferably 24–31; b is an integer from 50–150, preferably 65–135; more preferably 70–120; c is an integer from 7–90, preferably 10–70; more preferably 15–45; x is 2.

The initiator (I) in Formula I is selected from the group consisting of propylene glycol, dipropylene glycol, ethylene glycol, and diethylene glycol, and glycerol, most preferably the initiator is propylene glycol.

The initiator (I) in Formula II is selected from the group consisting of propylene glycol, dipropylene glycol, ethylene glycol, and diethylene glycol. Preferably the initiator is propylene glycol.

In Formula I and II, EO is ethylene oxide

In Formula I and II, AO is an alkylene oxide moiety having 3–4 carbons, preferably, said alkylene oxide moiety is propylene oxide or butylene oxide, most preferably propylene oxide.

Further, EO and AO in Formula I can be distributed randomly and/or arranged in a block sequence. In Formula II, the distribution must be random.

In Formula I and II, M is H or a cation selected from the group including but not limited to lithium, calcium, potassium, and cesium, most preferably potassium or hydrogen.

Description of the Method of Preparation of the Liquid Polyalkylene Glycol Carrier and Liquid Polyoxyalkylene Compound Miscible in Said Liquid Polyalkylene Glycol Carrier of the Present Invention Preparation Of the Liquid Polyoxyalkylene Compound of the Invention The liquid polyoxyalkylene compound of the invention was prepared by conventional techniques in 1 or 2 gallon stainless steel autoclaves that were equipped with stirring, pressure gauge, thermocouple and addition tube. For instance, an initiator, in all cases propylene glycol, and catalyst were vacuum stripped in a stainless steel stirred autoclave at 120° C. to remove water. The formation of a alkylene oxide block was achieved by the addition of propylene oxide at 105° C. under a nitrogen atmosphere with addition rates set such that the overall pressure does not exceed 90 psig. To the polyoxypropylene block was added a mixture of ethylene oxide and propylene oxide to form a mixed oxide hydrophilic block. Mixed oxide additions were carried out at 135° C. with the same pressure constraints as above. The final products were neutralized by addition of 85% phosphoric acid and inhibited by addition of 100 ppm t-butylhydroxytoluene.

Preparation of the Liquid Polyalkylene Glycol Carrier of the Invention

A two gallon stainless steel autoclave was charged with 1089 g of propylene glycol, 46.6 g of 45% potassium hydroxide and purged with nitrogen. The contents were heated to 80° C. and stripped to remove volatiles for 2 hours. The contents were heated to 130° C. and 4412.9 g of Ethylene oxide added over a period of six hours. After the addition was finished the mixture was kept at 130° C. for one hour and then volatiles stripped for ½ hour.

A five gallon stainless steel autoclave was charged with 3075.6 g of the above material and purged with nitrogen. The material was heated to 116° C. and 11,168 g of a mixture of 76.8% Ethylene Oxide and 23.2% Propylene Oxide added over a period of 9.5 hours. After the addition was complete, the mixture was kept at 116° C. for an additional two hours. A final charge of 1762 g of Ethylene Oxide was added over two hours and then kept at 116° C. for 2.5 hours. The mixture was stripped for ½ hour, cooled to 80° C. and 30.1 g of 50% Hypophosphorous acid added. The mixture was agitated for ½ hour in the autoclave and then discharged.

The Utility of the Present Invention

In order to illustrate the utility of the present invention, Applicants prepared binary blends comprising a liquid polyalkylene glycol and a high molecular weight, solid block copolymer with a molecular weight greater than 8000. Said binary blends were then compared to blends of the present invention comprising Compound A of Formula II (liquid) and Compound B of Formula I (liquid). See Table-1

The binary (solid /liquid) blends were prepared by first mixing the solid block copolymer with the liquid polyalkylene glycol and then heating the blend above the melting point of the solid block copolymer to obtain a clear, single phase composition. The resulting clear composition was then gradually allowed to cool to ambient temperatures while being continually stirred at 100 rpm on a LIGHTNIN mixer. The final composition was then stored at ambient temperatures and physical stability of the composition was noted.

The binary (liquid/liquid) blends of the present invention were prepared by simply mixing the components (a) liquid polyalkylene glycol carrier, and (b) liquid polyalkylene compound as defined hereinabove.

As the Table 1 indicates, all blends comprising a liquid, polyethylene glycol of molecular weight 400 and the solid, block copolymer were unstable on storage and separated into two phases. This is particularly evident when the samples are stored at 45° C. Clearly, Test 8 and 9 ( the present invention) illustrates the utility of the present invention in maintaining the stability and uniformity of dentrifice formulations.

However, when the solid block copolymer was replaced with the liquid polyoxyalkylene compound of Formula II (Compound A), then solubility was instantaneous and the resulting composition was a single phase, clear, stable, homogenous liquid. The table further shows that when the liquid, polyethylene glycol of molecular weight 400 is replaced with the liquid polyalkylene glycol of Formula I (Compound B), a clear, single phase, stable, homogenous composition is achieved upon blending with the liquid

TABLE 1

| Test # | Component A | Component B | Remarks | Stability |
|---|---|---|---|---|
| 1 | PEG 400 | Pluronic F38 | Heat to dissolve | Two phases - Unstable |
| 2 | PEG 400 | Pluronic F68 | Heat to dissolve | Two phases - Unstable |
| 3 | PEG 400 | Pluronic F87 | Heat to dissolve | Two phases - Unstable |
| 4 | PEG 400 | Pluronic F88 | Heat to dissolve | Two phases - Unstable |

TABLE 1-continued

| Test # | Component A | Component B | Remarks | Stability |
|---|---|---|---|---|
| 5 | PEG 400 | Pluronic F98 | Heat to dissolve | Two phases - Unstable |
| 6 | PEG 400 | Pluronic F108 | Heat to dissolve | Two phases - Unstable |
| 7 | PEG 400 | Pluronic F127 | Heat to dissolve | Two phases - Unstable |
| 8 | PEG 400 | Compound A of Formula II | Readily dissolves | Clear, single phase - Stable |
| 9 | Compound B of Formula | Compound A of Formula | Readily dissolves | Clear, single phase - Stable |

In each blend, the weight ratio of the liquid polyalkylene glycol to the solid block copolymer or Component B was 90:10.

Explanation of terms in Table 1

PEG400 - Liquid polyethylene glycol of molecular weight 400. Available from BASF Corporation as PLURACOL E-400 polyethylene glycol.

PLURONIC® is a registered trademark of BASF. Pluronic surfactant is a triblock copolymer of ethylene oxide and propylene oxide available from BASF. Pluronic F surfactant refers to the solid, triblock copolymers of ethylene oxide and propylene oxide.

PLURONIC(® F38 surfactant is a solid, triblock copolymer of ethylene oxide and propylene oxide with a average molecular weight of 4700.

PLURONIC® F68 surfactant is a solid triblock copolymer of ethylene oxide and propylene oxide with a average molecular weight of 8400.

PLURONIC® F87 is a solid triblock copolymer of ethylene oxide and propylene oxide with a average molecular weight of 7700.

PLURONIC® F88 is a solid triblock copolymer of ethylene oxide and propylene oxide with a average molecular weight of 11400.

PLURONIC® F98 is a solid triblock copolymer of ethylene oxide and propylene oxide with a average molecular weight of 13000.

PLURONIC® F108 is a solid triblock copolymer of ethylene oxide and propylene oxide with a average molecular weight of 14600.

PLURONIC® F127 is a solid triblock copolymer of ethylene oxide and propylene oxide with a average molecular weight of 12600.

Compound A of Formula II, wherein I is propylene glycol, AO is propylene oxide, and a is 29, b is 78, c is 15, and x is 2, and M is hydrogen.

Compound B of Formula I, wherein I is propylene glycol, AO is propylene oxide, and a is 18, b is 3, and M is hydrogen.

Preparation of Dentrifice Compositions Containing the Liquid Polyalkylene Glycol Carrier and Liquid Polyoxyalkylene Compound Miscible in Said Liquid Polyalkylene Glycol Carrier of the Present Invention The liquid polyalkylene glycol carrier and liquid polyoxyalkylene compound miscible in said liquid polyalkylene glycol carrier of the present invention are present in dentrifice compositions at a preferred level of 1–99%, more preferably at a level of 20–79%; most preferably at a level of 30–50% by weight of the dentrifice composition. Generally, the level of incorporation depends on the end use of the liquid polyalkylene compound of the invention. If they function as carriers, for example, in a essentially non-aqueous dentrifice formulation, then higher use levels are required in the formulation.

Dentrifice formulations also contain other ingredients such as surfactants selected from anionic surfactants which include sodium lauryl sulphate; sodium alkyl glyceryl ether sulfonate; alkyl benzene sulfonates. Other anionic surfactants also include oxyalkylates of $C_6$–$C_{18}$ alcohols. It is also known to those skilled in the art to use solid block copolymers of polyoxyethylene and polyoxypropylene to further provide a boost in the foaming performance of the dentrifice composition. Such solid block copolymers of ethylene oxide and propylene oxide are excluded from the scope of this invention. Further, small amounts of cationic surfactants, having a quaternary nitrogen, which show compatibility with the nonionic carrier blends of this invention can also be used. Various other materials may also be used in the formulating of personal care products. For example, peroxygen compounds such as hydrogen peroxide, sodium percarbonate, can be used in such dentrifice compositions. Dental abrasives consisting of finely divided silica, or calcium carbonate, sodium bicarbonate, calcium pyrophosphate, and hydrated alumina are added for polishing performance. Additionally, thickening agents such as collodial silica, xanthan gum, gum arabic, hydroxyethylcellulose, polyvinylpyrrolidone, gum tragacanth, carragennan can also be used to provide sufficient thickening consistency to the formulation. Also, flavoring agents such as peppermint, spearmint oils or preservatives, opacifying agents, buffer salts, sweeteners, anti-bacterial agents anti-calculus agents or anti-plaque agents, anti-inflammatory agents, anti-caries agents such as the fluoride salts can also be included in small amounts. Polymeric agents which accelerate the transport of active materials can also be included. Additionally, dentrifice compositions may contain small amounts of water.

Personal care products, such as dentrifices, are formulated according to methods known to those skilled in the art. Representative personal care product formulations are disclosed in: *Cosmetics, Science and Technology,* 2nd Edition, Vol. 1, Edited by M. S. Balsam, et al., and *A Formulary of Cosmetic Preparations,* Michael and Irene Ash, Chemical Publishing, N.Y., N.Y., both incorporated by reference herein.

The following non-limiting Example serves to illustrate the utility of the present invention. All percentages are weight percent (%) of the total composition unless otherwise indicated.

Dentrifice Composition:

- 1–55% abrasive, selected from the group including, but not limited to, anhydrous dicalcium phosphate, calcium carbonate, calcium pyrophosphate and sodium bicarbonate.
- 0–0.6% of a fluoridating agent, including, but not limited to stannous fluoride, sodium fluoride, sodium monoofluorophosphate.
- 2–10% binders, including, but not limited to, gum karaya, tragacanth USP, sodium alginate; Irish moss and methyl cellulose.
- 0–5% thickening agent, including but not limited to collodial silica.

0–10% of a peroxygen source, including but not limited to hydrogen peroxide, sodium percarbonate.

0–8% surfactants, including, but not limited to, sodium lauryl sulfate, sodium-N-lauryl sarcosinate; dioctyl sodium sulfosuccinate.

0.1–10% of the liquid polyoxyalkylene compound (b) represented by Formula II:

$$I[(AO)_a\text{-}(XO)\text{-}M]_x \qquad \text{Formula II}$$

wherein in Formula II:
I is an initiator or a mixture of initiators having at least two carbon atoms and two hydroxyl substituents;
AO is a $C_{3-4}$ alkylene oxide or mixtures of $C_{3-4}$ alkylene oxide arranged in a block sequence;
XO is $(EO)_b(AO)_c$ wherein EO is ethylene oxide and EO and AO are distributed randomly;
M is hydrogen or an alkali metal or an alkaline earth metal;
a is an integer from 15–35;
b is an integer from 50–150;
c is an integer from 7–90;
x is 2;

5–70% carriers selected from the group including but not limited to glycerin; propylene glycol; sorbitol; liquid polyethylene glycol, and the liquid polyalkylene glycols (a) represented by Formula I $$I\text{-}[(EO)_a(AO)_b\text{-}M]_x; \qquad \text{Formula I}$$

wherein in Formula 1, I is an initiator or a mixture of initiators having at least two carbon atoms and at least two or more hydroxyl substituents;
AO is a $C_{3-4}$ alkylene oxide or a mixture of $C_{3-4}$ alkylene oxides;
EO is ethylene oxide;
wherein, further EO and AO can be distributed randomly and/or arranged in a block sequence.
M is Hydrogen or an alkali metal or alkaline earth metal;
a is an integer from about 6–22;
b is an integer from about 1–9;
x is an integer from about 2–4;

We claim:

1. An oral care composition comprising:
   (a) a liquid polyalkylene glycol carrier and;
   (b) a liquid polyoxyalkylene compound miscible in said liquid polyalkylene glycol carrier, wherein said:
   liquid polyalkylene glycol carrier (a) is selected from the group consisting of:
      (i) liquid polyethylene glycols having a molecular weight of no more than about 600;
      (ii) liquid polyoxyalkylene glycols having a molecular weight greater than 600 and less than about 3000 of Formula I or mixtures of (I) and (ii):

$$I\text{-}[(EO)_a(AO)_b\text{-}M]_x; \qquad \text{Formula I}$$

wherein in Formula I, I is an initiator or a mixture of initiators having at least two carbon atoms and at least two or more hydroxyl substituents;
AO is a $C_{3-4}$ alkylene oxide or a mixture of $C_{3-4}$ alkylene oxides;
EO is ethylene oxide;
wherein, further EO and AO can be distributed randomly and/or arranged in a block sequence.
M is Hydrogen or an alkali metal or alkaline earth metal;
a is an integer from about 6–22;
b is an integer from about 1–9;
x is an integer from about 2–4;
further provided that;
said liquid polyoxyalkylene compound (b), which is miscible in (a), is represented by Formula II:

$$I[(AO)_a\text{-}(XO)\text{-}M]_x \qquad \text{Formula II}$$

wherein Formula II:
I is an initiator or a mixture of initiators having at least two carbon atoms and two hydroxyl substituents;
AO is a $C_{3-4}$ alkylene oxide or mixtures of $C_{3-4}$ alkylene oxide arranged in a block sequence;
XO is $(EO)_b(AO)_c$ wherein EO is ethylene oxide and EO and AO are distributed randomly;
M is hydrogen or an alkali metal or an alkaline earth metal;
a is an integer from 15–35;
b is an integer from 50–150;
c is an integer from 7–90;
x is 2.

2. A composition according to claim 1, wherein in Formula I, a is 7–20; b is 1–7; x is 2; I is propylene glycol; AO is propylene oxide and M is hydrogen.

3. A composition according to claim 1, wherein in Formula II, a is 20–32; b is 65–135; c is 10–70; x is 2; I is propylene glycol; AO is propylene oxide.

4. A composition according to claim 1, wherein in Formula I, a is 10–16; b is 2–5; and in Formula II, a is 24–31; b is 70–120; c is 15–45.

5. A dentifrice composition comprising:
   1–55% abrasive, selected from the group consisting of anhydrous dicalcium phosphate, calcium carbonate calcium pyrophosphate and sodium bicarbonate,
   0–0.6% of a fluoridating agent, selected from the group consisting of stannous fluoride, sodium fluoride, and sodium monoofluorophosphate
   2–10% binders selected from the group consisting of gum karaya, tragacanth USP, sodium alginate; Irish moss and methyl cellulose,
   0–5% thickening agent selected from the group consisting of collodial silica;
   0–10% of a peroxygen source selected from the group consisting of hydrogen peroxide and sodium percarbonate
   0–8% surfactants selected from the group consisting of sodium lauryl sulfate, sodium-N-lauryl sarcosinate; and dioctyl sodium sulfosuccinate,
   0.1–10% of the liquid polyoxyalkylene compound (b) represented by Formula II:

$$I[(AO)_a\text{-}(XO)\text{-}M]_x \qquad \text{Formula II}$$

wherein in Formula II:
I is an initiator or a mixture of initiators having at least two carbon atoms and two hydroxyl substituents;
AO is a $C_{3-4}$ alkylene oxide or mixtures of $C_{3-4}$ alkylene oxide arranged in a block sequence;
XO is $(EO)_b(AO)_c$ wherein EO is ethylene oxide and EO and AO are distributed randomly;
M is hydrogen or an alkali metal or an alkaline earth metal;
a is an integer from 15–35;
b is an integer from 50–150;
c is an integer from 7–90;
x is 2;

5–70% carriers selected from the group consisting of glycerin; propylene glycol; sorbital; liquid polyethylene glycol, and the liquid polyalkylene glycols (a) represented by Formula:

$$\text{I}-[(\text{EO})_a(\text{AO})_b-\text{M}]_x; \qquad \text{Formula I}$$

wherein in Formula I, I is an initiator or a mixture of initiators having at least two carbon atoms and at least two or more hydroxyl substituents;

AO is a $C_{3-4}$ alkylene oxide or a mixture of $C_{3-4}$ alkylene oxides;

EO is ethylene oxide;

wherein, further EO and AO can be distributed randomly and/or arranged in a block sequence;

M is Hydrogen or an alkali metal or alkaline earth metal;

a is an integer from about 6–22;

b is an integer from about 1–9;

x is an integer from about 2–4.

* * * * *